United States Patent [19]
Borders

[11] Patent Number: 6,149,674
[45] Date of Patent: Nov. 21, 2000

[54] PATIENT THERMAL REGULATION SYSTEM

[75] Inventor: Richard L. Borders, Cincinnati, Ohio

[73] Assignee: Hill-Rom, Inc., Batesville, Ind.

[21] Appl. No.: 09/187,989

[22] Filed: Nov. 6, 1998

Related U.S. Application Data

[60] Provisional application No. 60/064,709, Nov. 7, 1997.

[51] Int. Cl.$^7$ ....................................................... A61F 2/00
[52] U.S. Cl. .......................... 607/96; 607/104; 607/108; 601/148; 602/14
[58] Field of Search ............................... 607/96, 108, 109, 607/110, 104, 112, 111; 602/13, 14; 606/20, 27; 601/148–152

[56] References Cited

U.S. PATENT DOCUMENTS

| | | |
|---|---|---|
| Re. 22,763 | 6/1946 | Clark . |
| 750,179 | 1/1904 | Foglesong . |
| 1,110,494 | 9/1914 | Kellogg . |
| 1,399,095 | 12/1921 | Webb . |
| 2,272,481 | 2/1942 | Rinkes et al. . |
| 2,415,455 | 2/1947 | Barnes et al. . |
| 2,582,648 | 1/1952 | Mowbray . |
| 2,606,996 | 8/1952 | Westerberg et al. . |
| 2,792,827 | 5/1957 | Gravin et al. . |
| 2,832,336 | 4/1958 | Davis et al. . |
| 3,094,983 | 6/1963 | MacLeod . |
| 3,186,404 | 6/1965 | Gardner . |
| 3,785,374 | 1/1974 | Lipson . |
| 3,789,853 | 2/1974 | Reinhard .................................. 128/399 |
| 3,854,156 | 12/1974 | Williams . |
| 3,869,594 | 3/1975 | Shively . |
| 3,918,458 | 11/1975 | Nethery . |
| 3,967,627 | 7/1976 | Brown ..................................... 128/399 |
| 3,993,053 | 11/1976 | Grossan . |
| 4,013,069 | 3/1977 | Hasty . |
| 4,029,087 | 6/1977 | Dye et al. . |
| 4,149,529 | 4/1979 | Copeland et al. . |
| 4,156,425 | 5/1979 | Arkans . |
| 4,168,063 | 9/1979 | Rowland . |
| 4,198,961 | 4/1980 | Arkans . |
| 4,207,875 | 6/1980 | Arkans . |
| 4,207,876 | 6/1980 | Annis . |
| 4,253,449 | 3/1981 | Arkans et al. . |
| 4,280,485 | 7/1981 | Arkans . |
| 4,281,647 | 8/1981 | Antypas . |
| 4,320,746 | 3/1982 | Arkans et al. . |
| 4,331,133 | 5/1982 | Arkans . |
| 4,335,726 | 6/1982 | Kolstedt ................................. 128/400 |
| 4,338,944 | 7/1982 | Arkans . |
| 4,370,975 | 2/1983 | Wright . |
| 4,372,297 | 2/1983 | Perlin . |
| 4,375,217 | 3/1983 | Arkans . |
| 4,396,010 | 8/1983 | Arkans . |
| 4,402,312 | 9/1983 | Villari et al. . |
| 4,476,867 | 10/1984 | Parks ..................................... 128/400 |
| 4,481,937 | 11/1984 | Arkans . |
| 4,574,812 | 3/1986 | Arkans . |

(List continued on next page.)

FOREIGN PATENT DOCUMENTS

| | | |
|---|---|---|
| 0 542 383 | 5/1993 | European Pat. Off. . |
| 0 757 907 A1 | 2/1997 | European Pat. Off. . |
| 0 821 928 A2 | 2/1998 | European Pat. Off. . |

Primary Examiner—Linda C. M. Dvorak
Assistant Examiner—Jocelyn Debra Ram
Attorney, Agent, or Firm—Bose McKinney & Evans LLP

[57] ABSTRACT

A system for regulating a core body temperature of a person includes a pressure applicator configured to apply negative or cyclical positive pressure to a portion of the person to vasodilate blood vessels of the person within the portion, a heating device configured to supply heat to the portion of the person, and a control apparatus. The control apparatus is coupled to the heating device and includes a controller configured to vary the amount of heat supplied by the heating device. The amount of heat supplied by the heating device is varied in response to a difference in temperature between a preset temperature programmed into the controller and an actual core body temperature of the patient received by the controller from a temperature sensor on the person such that the controller maintains the actual core body temperature of the person at substantially the preset temperature.

38 Claims, 4 Drawing Sheets

U.S. PATENT DOCUMENTS

| | | |
|---|---|---|
| 4,638,392 | 1/1987 | Cartier et al. . |
| 4,747,409 | 5/1988 | Silen ........................................ 128/402 |
| 4,773,397 | 9/1988 | Wright et al. . |
| 4,858,596 | 8/1989 | Kolstedt et al. . |
| 4,938,208 | 7/1990 | Dye . |
| 5,007,411 | 4/1991 | Dye . |
| 5,031,604 | 7/1991 | Dye . |
| 5,034,006 | 7/1991 | Hosoda et al. . |
| 5,074,285 | 12/1991 | Wright . |
| 5,117,812 | 6/1992 | McWhorter . |
| 5,169,384 | 12/1992 | Bosniak et al. ............................ 604/20 |
| 5,186,163 | 2/1993 | Dye . |
| 5,251,347 | 10/1993 | Hopper et al. . |
| 5,263,473 | 11/1993 | McWhorter . |
| 5,342,285 | 8/1994 | Dye . |
| 5,369,807 | 12/1994 | Cho et al. . |
| 5,370,674 | 12/1994 | Farrell ........................................ 607/96 |
| 5,415,618 | 5/1995 | Koch ........................................... 600/22 |
| 5,449,379 | 9/1995 | Hadtke ...................................... 607/104 |
| 5,522,871 | 6/1996 | Sternlicht . |
| 5,609,619 | 3/1997 | Pompei . |
| 5,626,556 | 5/1997 | Tobler et al. . |
| 5,658,325 | 8/1997 | Augustine . |
| 5,683,438 | 11/1997 | Grahn . |
| 5,795,312 | 8/1998 | Dye . |
| 5,871,526 | 2/1999 | Gibbs et al. ............................. 607/104 |
| 5,913,886 | 6/1999 | Soloman ................................. 607/108 |
| 5,957,830 | 9/1999 | Skulic ........................................ 600/22 |

PATIENT THERMAL REGULATION SYSTEM

BACKGROUND AND SUMMARY OF THE INVENTION

This application claims the benefit of U.S. Provisional Application Ser. No. 60/064,709 filed Nov. 7, 1997.

The present invention relates to a patient thermal regulation system configured to regulate the core body temperature of a patient during a surgical procedure. More particularly, the present invention relates to a patient thermal regulation system that applies regulated heat to an extremity of a patient that is being cyclically compressed.

According to one aspect of the present invention, a method is provided for regulating an actual core body temperature of a person. The method includes the steps of setting a desired core body temperature of the person, measuring the actual core body temperature of the person, and comparing the actual core body temperature of the person to the desired core body temperature of the person. The core body temperature of the person is adjusted by vasodilating blood vessels of a portion of the person to promote absorption and transfer of heat from the portion of the person to the core body of the person and applying heat to the portion of the person simultaneously with the vasodilating step. By adjusting the amount of heat applied in the applying step based on the comparing step, the person's core body temperature is regulated to substantially the desired core body temperature.

In one illustrated embodiment, the method includes vasodilating the blood vessels by applying cyclical positive pressure to a medium pumped into a sleeve covering the calf area of the person. In another illustrated embodiment of the invention, pre-warmed intravenous solution is pumped into the blood vessels of the person to prevent a reduction in the core body temperature due to the introduction of the intravenous solution. In further embodiments of the invention, a thermal material engaging the portion of the person provides heat to the portion of the person during the applying step, the temperature of the intravenous solution is automatically adjusted based on the results of the comparing step, and the medium inflating the sleeve is cyclically pumped into the sleeve to apply a cyclical positive pressure to the sleeve during the vasodilating step.

According to another aspect of the present invention, a system is provided for regulating a core body temperature of a person. The system includes a pressure applicator configured to apply pressure to a portion of the person to vasodilate blood vessels of the person within the portion, a heating device configured to supply heat to the portion of the person, and a control apparatus. The control apparatus is coupled to the heating device and includes a controller configured to vary the amount of heat supplied by the heating device. The amount of heat supplied by the heating device is varied in response to a difference in temperature between a preset temperature programmed into the controller and an actual core body temperature of the patient received by the controller from a temperature sensor on the person such that the controller maintains the actual core body temperature of the person at substantially the preset temperature.

In one illustrated embodiment of the present invention the pressure applicator is a sleeve covering the portion of the person which is supplied with a medium supplied at a cyclical positive pressure by a pressure generator causing the sleeve to apply cyclical pressure to the portion of the person. In another illustrated embodiment of the present invention the pressure applicator applies negative pressure to the portion of the person. In another illustrated embodiment the controller controls the cyclically compression so that it is at a rate corresponding to the heart rate of the person. In still another embodiment, the heating device is a conductive fabric disposed between the pressure applicator and the portion of the patient so that the fabric supplies heat to the portion of the patient upon the application of a voltage to the fabric. In yet another embodiment of the invention the system includes an intravenous device which supplies a pre-warmed intravenous solution to the person.

According to yet another aspect of the present invention, a control apparatus is provided for regulating an actual core body temperature of a patient using a sleeve configured to cover an extremity of the patient. The apparatus includes a housing, an input device coupled to the housing and configured to allow a user to input a desired core body temperature for the patient, and a controller. The controller is contained within the housing and electrically coupled to the input device to allow the controller to receive the desired temperature. The controller is configured to supply a medium to the sleeve to provide a pressure on the extremity of the patient to vasodilate blood vessels in the extremity. The controller is also configured to receive an input indicating the actual core body temperature from a temperature sensor on the patient and to compare the desired temperature to the actual core body temperature of the patient measured by the temperature sensor on the patient and to vary the heat of the medium supplied to the sleeve based upon any difference between the actual core body temperature and the desired core body temperature. The control apparatus regulates the actual core body temperature of the patient to substantially the desired temperature.

In one illustrated embodiment of the invention, the controller also controls a supply of pre-warmed intravenous solution to the patient. The controller may be configured to regulate the temperature of the intravenous solution based on the actual core temperature of the patient. In another embodiment of the invention, the apparatus supplies air to the sleeve under negative pressure or cyclical positive pressure to vasodilate blood vessels in the portion of the patient.

According to still another aspect of the present invention, a system is provided for regulating the core body temperature of a person. The system includes a sleeve configured to cover a portion of the person, and a tube coupled at one end to the sleeve and at the other end to a control apparatus. The control apparatus includes a controller configured to supply a medium through the tube to the sleeve to cause the sleeve to cyclically compress the portion of the person to vasodilate the blood vessels in the portion of the person. The controller is configured to vary the heat of the medium in response to a difference in temperature between a preset temperature programmed into the controller and an actual core body temperature of the patient as measured by a temperature sensor on the person. The controller maintains the core body temperature of the patient at substantially the preset temperature.

Additional features of the present invention will become apparent to those skilled in the art upon consideration of the following detailed description of the presently perceived best mode of carrying out the invention.

BRIEF DESCRIPTION OF THE DRAWINGS

The detailed description particularly refers to the accompanying figures in which.

DETAILED DESCRIPTION OF THE DRAWINGS

Figure 1:
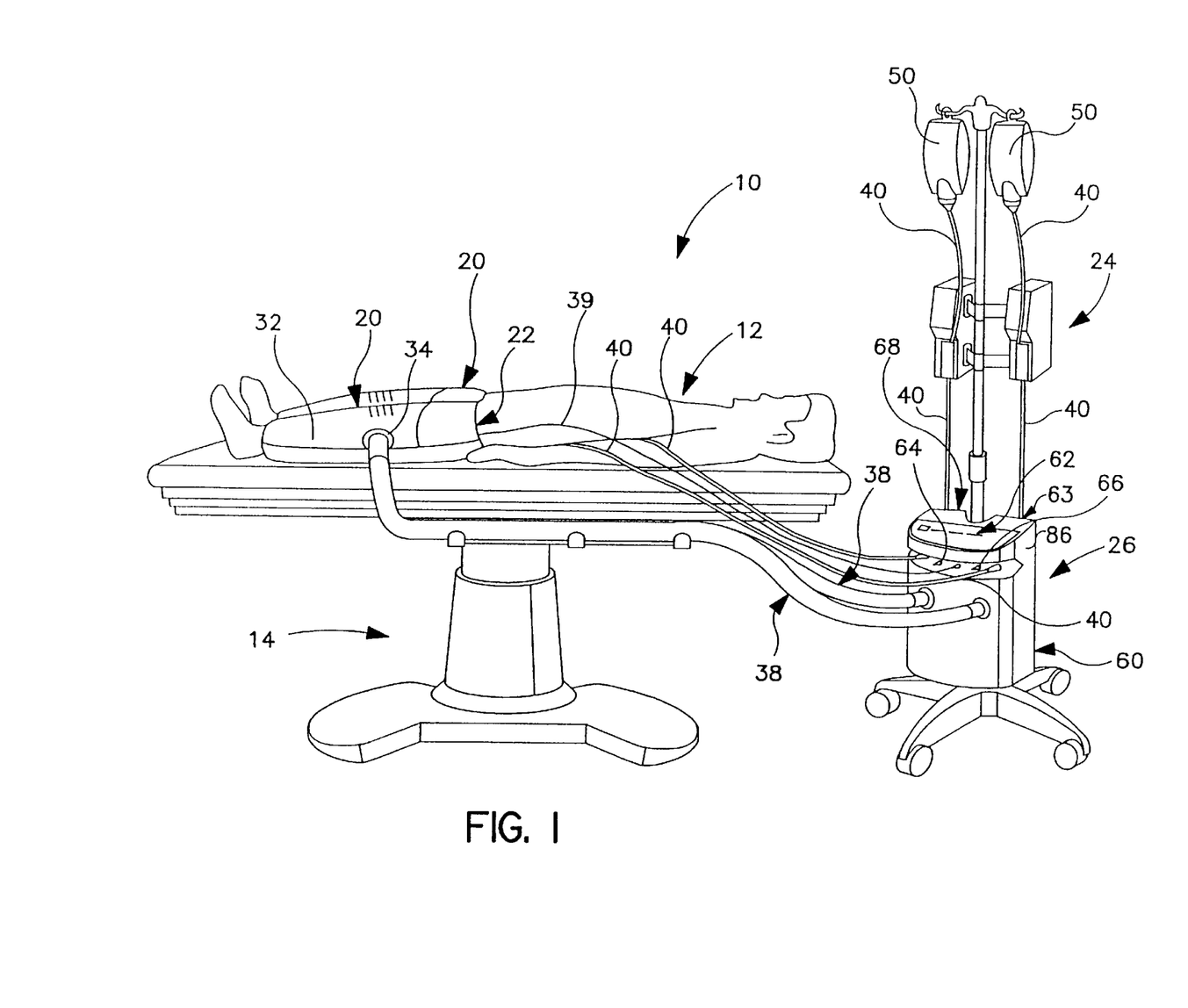
FIG. 1 is a perspective view of an illustrative system for regulating a core body temperature of a person in accordance with the present invention showing the system including a control apparatus mounted to a cart which also includes an intravenous supply system, a sleeve worn on each leg of the person, and a tube extending from each sleeve to the control apparatus to allow the control apparatus to control a flow of a medium through the tubes to the sleeves.

Referring now to the drawings, FIG. 1 illustrates a regulation system 10 configured to regulate a core body temperature of a patient 12 lying on an operating room table 14. The regulation system 10 includes a pressure applicator 20, a heating/cooling device 22, an intravenous device 24, and a control apparatus 26. The pressure applicator 20 is configured to apply either a negative pressure or a cyclical positive pressure to a portion (i.e., an extremity) of the patient 12 so that the blood vessels in the extremity vasodilate to promote heat absorption and transfer from the extremity to the patient's core body. The heating/cooling device 22 is then used to provide regulated heating or cooling to the extremity of the patient 12 so that the core body temperature of the patient 12 is controlled. The intravenous device 24 prevents a reduction in the core body temperature of patient 12 by permitting a pre-warmed intravenous solution 50 to be injected into the blood vessels of the patient 12. The control apparatus 26 controls the pressure applicator 20, heating/cooling device 22, and intravenous device 24 to regulate the core body temperature of the patient 12 as described below.

As shown in FIG. 1, pressure applicator 20 is preferably a sleeve that is configured to slide over an extremity of patient 12 such as any part of a leg or arm including the hands and the feet. (Note: two sleeves 20 are shown in FIG. 1, one sleeve 20 for each leg.) The sleeve 20 is configured to receive a medium (not shown) from a pressure generator 86 contained within control apparatus 26 so that a pressure, either negative or cyclical positive, can be applied to the portion of patient 12 covered by sleeve 20. The sleeve 20 includes a shell portion 32 defining an interior region (not shown) and an inlet portion 34. Inlet portion 34 is configured to allow the medium to enter the interior region so that the shell portion 32 expands or contracts to apply the negative or cyclical positive pressure to the portion of patient 12 enclosed by sleeve 20.

In the illustrated embodiment, the medium enters the interior region of the sleeve 20 under cyclical positive pressure so that the shell portion 32 presses against the portion of patient 12 covered by sleeve 20 cyclically. This cyclical pressure of sleeve 20 around the extremity of patient 12 vasodilates the blood vessels of the patient 12 in the extremity to promote absorption and transfer of heat from the extremity to the core body of the patient 12. Of course, sleeve 20 could also be configured to apply a negative pressure to an extremity of patient 12 in order to vasodilate the blood vessels of the patient 12. In addition, the cyclical pressure may be matched to the heart rate of patient 12 as described below. The cyclical pressure may also be applied sequentially along the length of the sleeve 20. Controls for such sequential compression devices are well known.

Each pressure applicator (or sleeve) 20 is coupled to the pressure generator 86 contained in control apparatus 26 using a tube 38, as shown in FIG. 1. The tube 38 allows the medium to be transferred from pressure generator 86 to sleeve 20. Preferably, the medium supplied by control apparatus 26 and transferred to sleeve 20 through tube 38 is air. However, any liquid or gaseous medium can be used that allows pressure applicator 20 to apply negative or cyclical positive pressure to a portion of a patient. In addition, the air is preferably supplied to sleeve 20 in cycles so that sleeve 20 cyclically compresses the portion of patient 12 covered by sleeve 20. As discussed below, control apparatus 26 can also be configured to match the cyclical compression of the sleeve 20 with the heart rate of patient 12. Although the pressure applicator 20 is described illustratively as a sleeve having the elements described above, any pressure applicator that applies pressure (cyclical positive or negative) to an extremity of a patient to vasodilate the blood vessels of that extremity of the patient could be used.

Heating/cooling device 22 is configured to heat or cool the portion of patient 12 being vasodilated by pressure applicator 20. Preferably, the heating/cooling device 22 is a thermal material (such as Gorix™ material) positioned between the pressure applicator 20 and the portion of the patient 12 being cyclically compressed, as shown in FIG. 1. The thermal material 22 is illustratively a heating element having a conductive fabric that allows low-voltage electricity to pass through the fabric to change the temperature of the fabric. The low voltage electricity passing through the Gorix material 22 causes the fabric to heat up in a uniform manner proportionally with voltage being applied.

A wire 39 is used to supply low-voltage electricity from the control apparatus 26 to the thermal material 22, as shown in FIG. 1. As described below, the control apparatus 26 supplies the appropriate amount of electrical voltage through wire 39 to thermal material 22 so that an appropriate amount of heat is applied to the extremity of patient 12 for regulating the core body temperature of patient 12.

Although the heating/cooling device 22 is described herein as being a thermal material having the elements described above, any heating/cooling device that provides heating or cooling to a portion of a patient being vasodilated by a pressure applicator could be used. For example, as shown by the dotted lines in FIG. 3, the heating/cooling of patient 12 is accomplished by a heating/cooling generator 88 coupled between a pressure generator 86 and pressure applicator 20. The heating/cooling generator 88 is configured to regulate the temperature of the medium passing through sleeve 20 so that sleeve 20 not only cyclically compresses the portion of patient 12 covered by sleeve 20, but also provides heating/cooling to the portion. Thus, a separate heating/cooling device 22 is not required when a heating/cooling generator 88 is used to heat/cool the medium passing through pressure applicator 20. In addition, numerous other heating/cooling devices can be used to provide heating or cooling of an extremity of a patient being vasodilated in accordance with the present invention.

Intravenous device 24 is configured to supply an intravenous solution 50 to control apparatus 26 so that solution 50 can be pre-warmed by control apparatus 26 before being admitted to patient 12. As shown in FIG. 1, solution 50 is admitted to patient 12 using an intravenous tube 40. Tube 40 extends through control apparatus 26 so that solution 50 can be warmed by control apparatus 26 as described below. Thus, the pre-warmed solution 50 supplied to patient 12 prevents a reduction in core body temperature of patient 12 because pre-warmed solution 50 enters the blood vessels of patient 12 at an appropriate temperature relative to the core body of patient 12. Although two intravenous solutions 50 and two tubes 40 are shown in FIG. 1, the intravenous solutions 50 may be identical to one another or different from one another and either solution or both solutions may be heated and/or regulated by control apparatus 26 as described below.

Figure 2:
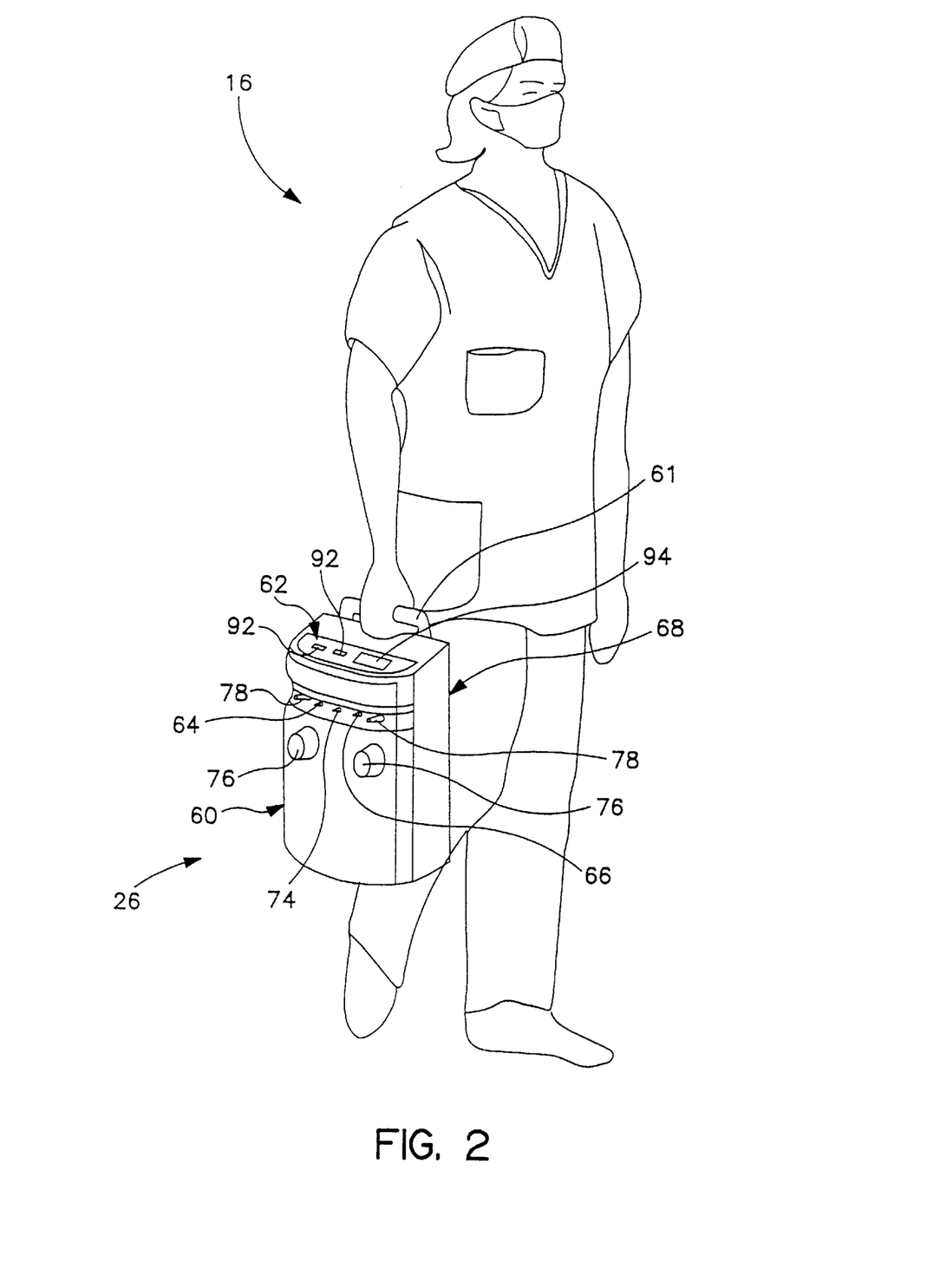
FIG. 2 is a perspective view of a nurse holding the control apparatus of FIG. 1 in one hand.
Figure 3:
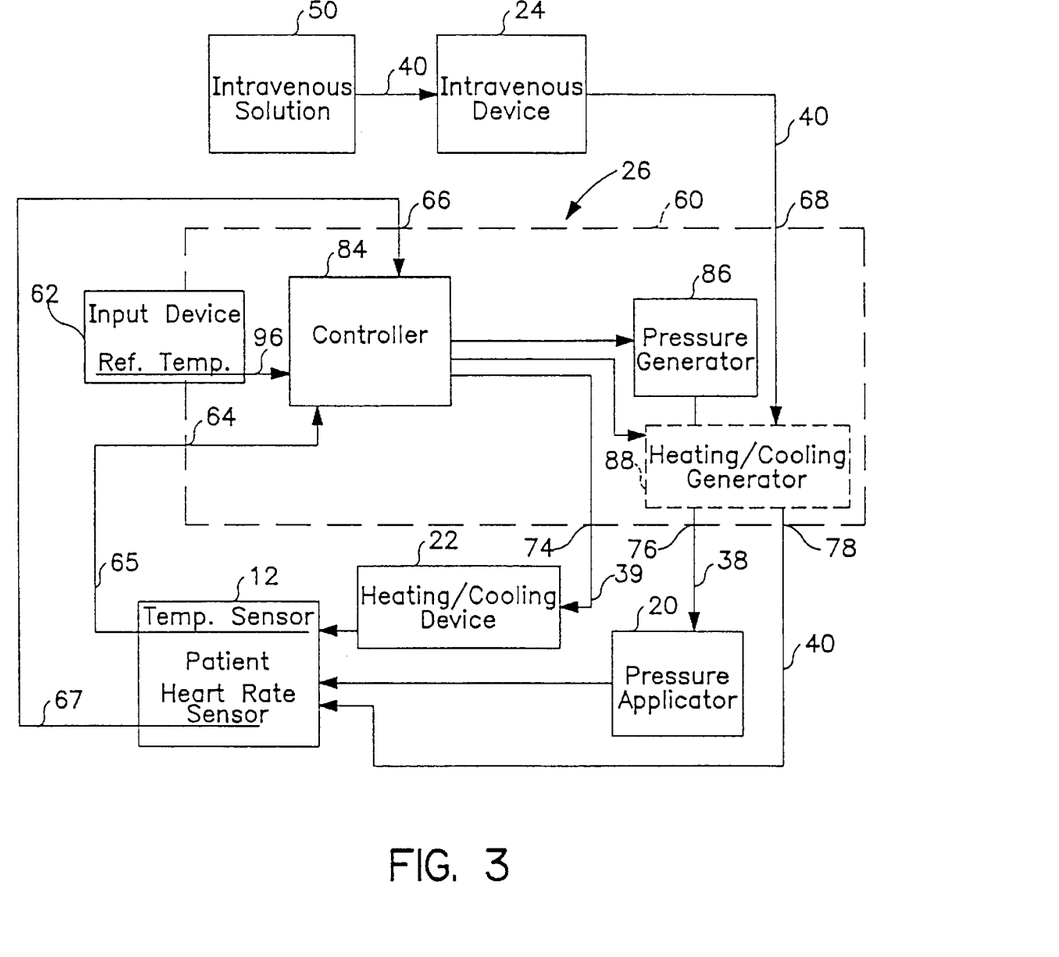
FIG. 3 is a block diagram illustrating details of the patient thermal regulation system.

Control apparatus 26 is configured to control pressure applicator 20, heating/cooling device 22, and intravenous device 24 to regulate the core body temperature of patient 12 automatically. As shown in FIGS. 1 and 2, control apparatus 26 includes a housing 60, an input device 62 mounted to an outer surface of housing 60, a plurality of input ports 64, 66, 68, and a plurality of output ports 74, 76, 78. In addition, as shown in FIG. 3, control apparatus 26 includes a controller 84, a pressure generator 86, and an optional (as shown by the dotted lines) heating/cooling generator 88 contained within housing 60.

Housing 60, as shown in FIGS. 1 and 2, is formed to be box-shaped and includes a handle 61. Handle 61 allows control apparatus 26 to be carried by a care giver 16 using one hand as shown in FIG. 2. In addition, the size and shape of box-shaped housing 60 allows control apparatus 26 to be easily moved from one location to another. The housing 60 may either be placed on the floor adjacent the table 14 or located on a cart as shown in FIG. 1.

Input device 62 is mounted to an outer surface of housing 60 of control apparatus 26. Input device 62 includes push buttons 92 and a display screen 94. Push buttons 92 allow care giver 16 to input information into input device 62 which is then transferred to controller 84 as shown in FIG. 3. In addition, display screen 94 displays to care giver 16 the status of various control functions and the values of the information input by care giver 16 using push buttons 92. Thus, as shown in FIG. 3, a care giver 16 can input a reference temperature 96 into input device 62 which is then transmitted to controller 84. Reference temperature 96 is then used by controller 84 to control heating/cooling device 22 and/or pressure applicator 20 to regulate the core body temperature of patient 12 as discussed below.

It is understood that the input device 62 may be a separate input device which is either tethered to the housing 60 or a separate wireless remote control device. An example of such remote control device is disclosed in U.S. application Ser. No. 09/187,825, entitled Medical Equipment Controller, filed Nov. 6, 1998 which is incorporated herein by reference.

Input ports 64, 66, 68 allow control apparatus 26 to receive various inputs relating to controlling the core body temperature of patient 12. For example, input port 64 is preferably a temperature sensor input coupled to controller 84 that allows controller 84 to receive an input corresponding to the core body temperature of patient 12, as shown in FIG. 3. Although not shown in FIG. 1, it is understood that temperature sensor input 64 is configured to receive any type of device capable of reading the core body temperature of patient 12 and transmitting that signal to controller 84. Thus, as shown in FIG. 3, a temperature sensor signal 65 on patient 12 is transmitted to controller 84 through temperature sensor input 64 such that temperature sensor signal 65 corresponds to an actual core body temperature of patient 12.

Input port 66 is preferably a heart rate sensor input 66 as shown in FIG. 3. Heart rate sensor input 66 allows a heart rate sensor signal 67 from patient 12 to be transmitted to controller 84 through heart rate sensor input 66. Once again, a heart rate sensor and heart rate sensor signal is not shown in FIG. 1, but it is understood that there are numerous devices that can accurately measure the heart rate of a patient and transmit it to controller 84.

Input port 68 is preferably an intravenous input that allows the tube 40 for supplying intravenous solution 50 to enter control apparatus 26 as shown in FIG. 3. Optional heating/cooling generator 88 is then configured to heat or cool the intravenous solution 50 in tube 40 based on control signals from controller 84 so that intravenous solution 50 is heated or cooled as needed before being supplied to patient 12.

Output ports 74, 76, 78 allow signals and mediums to be outputted from control apparatus 26 to patient 12 to control the core body temperature of patient 12. Output port 74 is preferably a heating/cooling device control output that allows controller 84 to control the heating or cooling of patient 12 by heating/cooling device 22. For example, when heating/cooling device 22 is a thermal material triggered by low-voltage electricity, output port 74 outputs a low-voltage signal to control the temperature of the thermal material 22. Output port 76 is illustratively a pressure generator output that allows controller 84 to control the amount of pressure applied to patient 12 by pressure applicator 20. As shown in FIG. 3, pressure generator output port 76 may be configured to allow the medium supplied by pressure generator 86 to pressure applicator 20 to be heated or cooled so that the pressure applicator 20 serves as a combined pressure applicator and heating/cooling device as discussed above. Finally, output port 78 is preferably an intravenous solution output that allows the tube 40 containing intravenous solution 50 to exit the control apparatus 26. Once again, optional heating/cooling generator 88 may be used to pre-warm intravenous solution 50 as intravenous solution 50 passes through control apparatus 26 such that controller 84 controls the temperature of intravenous solution 50 as it is received by patient 12.

Controller 84 is configured to control pressure generator 86, optional heating/cooling generator 88, and heating/cooling device 22, as shown in FIG. 3, to regulate the core body temperature of patient 12 automatically. First, controller 84 may be configured to control pressure generator 86 so that the cyclical positive pressure being applied by pressure applicator 22 is matched to the heart rate of patient 12. Thus, heart rate sensor signal 67 is inputted into controller 84 and controller 84 transmits the appropriate signal to pressure generator 86 to permit pressure generator 86 to trigger pressure applicator 20 to apply pressure to patient 12 at the same rate as the heart rate of patient 12. However, it is understood that pressure generator 86 may be located as a separate device outside of control apparatus 26 and configured to apply a signal to pressure applicator 20 so that pressure is not matched with the heart rate of patient 12.

Controller 84 also controls optional heating/cooling generator 88 to control the temperature of the medium being generated by pressure generator 86 and transmitted to pressure applicator 20 and/or controlling the temperature of intravenous solution 50. Illustratively, when optional heating/cooling generator 88 is used, pressure generator 86 transmits a fluid medium to heating/cooling generator 88. Heating/cooling generator 88 then heats or cools the fluid medium to increase or decrease the core body temperature of patient 12 as needed. Pressure generator 86 also supplies the fluid medium through heating/cooling generator 88 to pressure applicator 20 in a cyclical manner so that pressure applicator 20 cyclically compresses a portion of patient 12. The cyclical compression may, but need not, match the heart rate of patient 12 or be applied sequentially along the length of sleeve 20. Thus, as shown in FIG. 1, sleeve 20 can be simultaneously compressed at a rate matching the heart rate of the patient using a liquid or gaseous medium while the temperature of the medium is regulated to match the core body temperature of patient 12 to a preset referenced temperature 96 inputted into controller 84 using input device 62.

Controller 84 may also be configured to control heating/cooling device 22 so that optional heating/cooling generator 88 is not needed. For example, when heating/cooling device 22 is a thermal material requiring a low voltage electricity source to control the temperature of the material, controller 84 can output a low voltage signal through output port 74 to control heating/cooling device 22 as needed.

Figure 4:
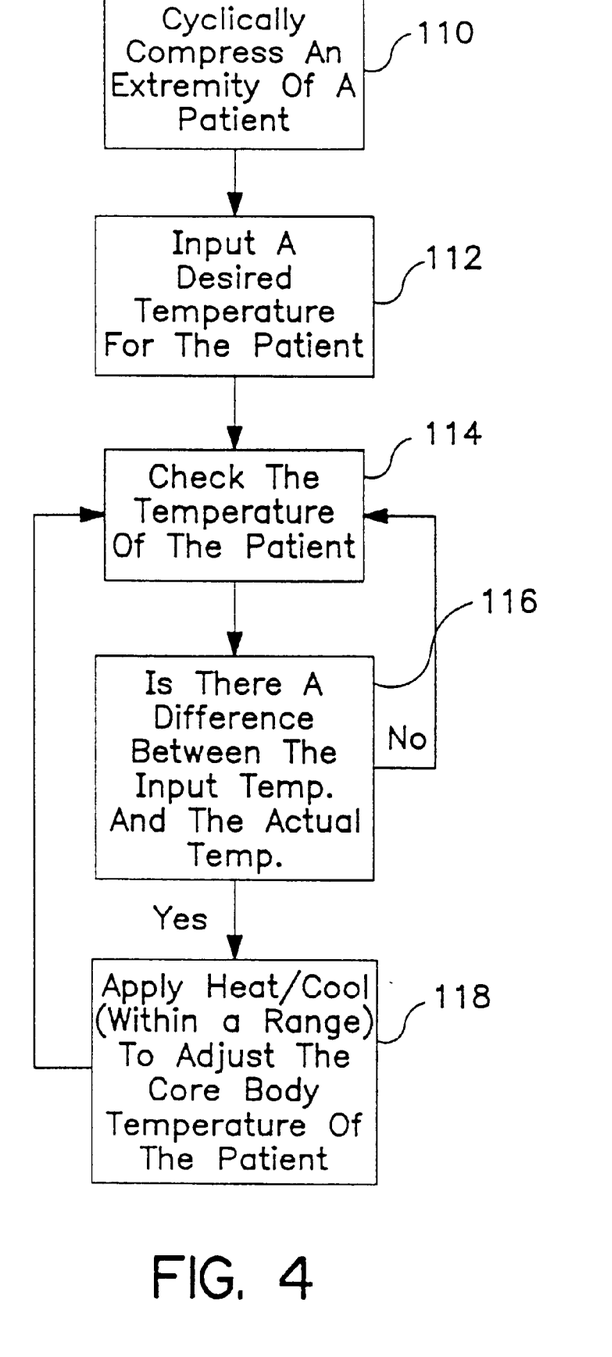
FIG. 4 is a flow diagram illustrating steps performed to regulate a patient's core body temperature.

In operation, controller 84 of control apparatus 26 regulates the core body temperature of patient 12 by performing the steps shown in FIG. 4. As illustrated by block 110, regulation system 10 first cyclically compresses an extremity of patient 12. Illustratively, this is performed by having pressure generator 86 transmit a medium in cycles to sleeve 20 so that sleeve 20 cyclically compresses the extremity of patient 12 covered by sleeve 20 to vasodilate blood vessels in the extremity. However, as mentioned above, any type of negative or cyclical positive pressure could be applied to a portion of patient 12 to vasodilate blood vessels within the portion of patient 12 using a wide variety of pressure generators and/or pressure applicators. A vacuum pump may be included in the control apparatus 26 as the pressure generator 86 if it is desired to apply negative pressure.

The next step, as illustrated by block 112 in FIG. 4, is to input a desired temperature for patient 12 into control apparatus 26. This is preferably accomplished by having caregiver 16 manually enter a desired core body temperature for patient 12 into input device 62 which then transmits the signal 96 to controller 84. However, the desired temperature need not be manually input by caregiver 16. Instead, a desired temperature could be preset into controller 84 so that an input device 62 would not be required.

The next step, as illustrated by block 114 in FIG. 4, is to check the temperature of patient 12. Illustratively, this is accomplished by having a temperature sensor coupled to patient 12 that measures the core body temperature of patient 12 and transmits the temperature signal to controller 84.

The next step, as illustrated by block 116 in FIG. 4, is for controller 84 to determine whether there is a difference between the reference temperature input by caregiver 16 and the actual core body temperature of patient 12. If there is no difference in temperature, controller 84 returns to block 114 to check the core body temperature of patient 12 and the loop continues until a temperature difference is detected.

When a difference in temperature between the input temperature and the actual core body temperature is detected at block 116, the next step, as illustrated by block 118 in FIG. 4, is to apply heat/cool to patient 12 to adjust the core body temperature of patient 12 to regulate the core body temperature of patient 12 to substantially the desired core body temperature. The amount of heat/cool applied to patient 12 is limited to a predefined range of temperatures so that too much heating or cooling is not applied to patient 12.

As described above, the compression thermal regulation system 10 distributes regulated temperature to a portion of a patient (such as the calf area) while simultaneously applying negative or cyclical positive pressure to the portion to promote transfer of heat from the portion to the core body of the patient. The regulation system 10 regulates patient temperature by maintaining proper circulatory system temperature, functions as a sequential pressure applicator only or as a compression/thermal regulation system, has a power unit/control system that mounts to standard intravenous stand or elsewhere, is upgradeable to intravenous warming system, and is configured to operate on a variety of temperature transfer points such as the arms and/or hands.

The compression thermal regulation system 10 regulates body temperature internally and noninvasively. The system 10 also integrates three key patient support systems (sequential compression, thermal regulation, and intravenous pre-warming) into one small system. The system further eliminates the need for cumbersome thermal drape systems (i.e., Bair Hugger) and reduces floor congestion by consolidating devices.

It is understood that the pressure generator 86 within control apparatus 26 may also be used to supply fluid to a patient support surface or mattress located on the operating room table 14. Details of an illustrative mattress are disclosed in U.S. patent application Ser. No. 09/188,785, entitled Surgical Table, filed Nov. 6, 1998 which is incorporated herein by reference.

Although the invention has been described in detail with reference to certain illustrated embodiments, variations and modifications exist within the scope and spirit of the invention as described and defined in the following claims.

What is claimed is:

1. A method for regulating an actual core body temperature of a person having a core body, a core body temperature, and blood vessels, the method comprising the steps of:

providing a controller and a temperature sensor, the temperature sensor being adapted to be coupled to the patient, setting a desired core body temperature of the person in the controller, measuring the actual core body temperature of the person using the temperature sensor, comparing, in the controller, the actual core body temperature of the person to the desired core body temperature of the person to determine if the core body temperature of the person needs to be adjusted, the comparing step being performed on an ongoing basis, vasodilating blood vessels of a portion of the person to promote absorption and transfer of heat from the portion of the person to the core body of the person, and one of heating or cooling the portion of the person if the comparing step determines that the core body temperature of the person needs to be adjusted.

2. The method of claim 1, wherein the vasodilating step includes applying a pressure to a sleeve covering the portion of the person.

3. The method of claim 2, wherein the pressure being applied is a negative pressure.

4. The method of claim 2, wherein the pressure is applied by cyclically pumping a medium into the sleeve.

5. The method of claim 4, wherein the medium is air.

6. The method of claim 4, wherein the heating or cooling step includes heating the medium traveling through the sleeve.

7. The method of claim 2, wherein the portion of the person is a calf area of the person.

8. The method of claim 1, further comprising the step of pumping a pre-warmed intravenous solution into the blood vessels of the person to prevent a reduction of the core body temperature.

9. The method of claim 8, wherein the setting, comparing, and adjusting steps are controlled by a hand-held control apparatus.

10. The method of claim 8, wherein a thermal material engaging the portion of the person is configured to provide heat to the portion of the person during the applying step.

11. The method of claim 8, wherein a conductive fabric engaging the portion of the person is configured to provide heat to the portion of the person during the applying step.

12. The method of claim 8, wherein a temperature of the intravenous solution is automatically adjusted based on the comparing step.

13. The method of claim 8, wherein the vasodilating step includes applying a cyclical positive pressure to a sleeve covering the portion of the person by cyclically pumping a medium into the sleeve to inflate the sleeve.

14. A system for regulating a core body temperature of a person having a core body temperature and blood vessels, the system comprising:
   a pressure applicator configured to apply pressure to a portion of the person to vasodilate blood vessels of the person within the portion,
   a heating and cooling device configured to heat and cool the portion of the person,
   a temperature sensor adapted to be coupled to the person, and
   a control apparatus coupled to the heating and cooling device, the control apparatus having a controller configured to vary the amount of heat and cool supplied by the heating and cooling device in response to a difference in temperature between a preset temperature programmed into the controller and an actual core body temperature of the person received by the controller from the temperature sensor on the person such that the controller maintains the actual core body temperature of the person at substantially the preset temperature.

15. The system of claim 14, wherein the pressure applicator is a sleeve covering the portion of the person.

16. The system of claim 15, wherein the control apparatus includes a pressure generator coupled between the controller and the sleeve and configured to supply a medium to the sleeve to cause the sleeve to apply pressure to the portion of the person.

17. The system of claim 16, wherein the pressure generator supplies the medium at a cyclical positive pressure to cause the sleeve to cyclically compress the portion of the person.

18. The system of claim 16, wherein the medium supplied by the pressure generator to the pressure applicator is a liquid.

19. The system of claim 15, wherein the sleeve applies negative pressure to the portion of the person.

20. The system of claim 14, wherein the pressure applicator is configured to cyclically compress the portion of the person.

21. The system of claim 20, wherein the pressure applicator is controlled by the controller to cyclically compress the portion of the person at a rate corresponding to a heart rate of the person.

22. The system of claim 20, wherein the heating and cooling device includes a conductive fabric adapted to be positioned between the pressure applicator and the portion of the person, the conductive fabric being configured to supply heat to the portion of the person upon application of an electrical voltage to the fabric.

23. A system for regulating a core body temperature of a person having a core body temperature and blood vessels, the system comprising:
   a pressure applicator configured to apply pressure to a portion of the person to vasodilate blood vessels of the person within the portion,
   a heating device configured to supply heat to the portion of the person, and
   a control apparatus coupled to the heating device, the control apparatus having a controller configured to vary the amount of heat supplied by the heating device in response to a difference in temperature between a preset temperature programmed into the controller and an actual core body temperature of the person received by the controller from a temperature sensor on the person such that the controller maintains the actual core body temperature of the person at substantially the preset temperature, the pressure applicator being configured to cyclically compress the portion of the person, the heating device being a conductive fabric adapted to be positioned between the pressure applicator and the portion of the person, the conductive fabric being configured to supply heat to the portion of the person upon application of an electrical voltage to the fabric, and the controller regulates the electrical voltage being supplied to the fabric.

24. The system of claim 14, wherein the heating and cooling device includes a conductive fabric positioned between the pressure applicator and the portion of the person, the conductive fabric being configured to supply heat to the portion of the person upon application of an electrical voltage to the fabric.

25. The system of claim 24, further comprising an intravenous device configured to supply a pre-warmed intravenous solution to the person.

26. The system of claim 24, wherein the pressure applicator is controlled by the controller to cyclically compress the portion of the person at a rate corresponding to the heart rate of the person.

27. A control apparatus for regulating an actual core body temperature of a patient using a sleeve configured to cover an extremity of the patient and a temperature sensor coupled to the patient, the patient having a core body temperature and blood vessels, the apparatus comprising:
   a housing,
   an input device coupled to the housing and configured to allow a user to input a desired core body temperature for the patient,
   a heating and cooling device configured to heat and cool the patient, and
   a controller contained within the housing and electrically coupled to the input device to allow the controller to receive the desired temperature, the controller being configured to supply a medium to the sleeve to provide a pressure on the extremity of the patient to vasodilate blood vessels in the extremity, the controller being configured to receive an input indicating the actual core body temperature from the temperature sensor on the patient and to compare the desired temperature to the actual core body temperature of the patient measured by the temperature sensor on the patient and being coupled to the heating and cooling device to vary the heat and cool of the medium supplied to the sleeve based upon any difference between the actual core body temperature and the desired core body temperature to regulate the actual core body temperature of the patient to substantially the desired temperature.

28. The apparatus of claim 27, wherein the controller is further configured to control a supply of a pre-warmed intravenous solution to the patient.

29. The apparatus of claim 28, wherein the controller is further configured to regulate the temperature of the pre-warmed intravenous solution based on the actual core body temperature of the patient.

30. The apparatus of claim 28, wherein the housing includes a handle and is configured to be held in one hand.

31. The apparatus of claim 27, wherein the medium is air.

32. The apparatus of claim 31, wherein the air supplied to the sleeve provides a positive cyclical pressure on the extremity of the patient to vasodilate blood vessels in the extremity.

33. The apparatus of claim 31, wherein the air supplied to the sleeve provides a negative pressure on the extremity of the patient to vasodilate blood vessels in the extremity.

34. The apparatus of claim 27, wherein the medium is a liquid.

35. A system for regulating the core body temperature of a person having a core body temperature and blood vessels, the system comprising a sleeve configured to cover a portion of a person, a tube having a first end coupled to the sleeve and a second end positioned away from the sleeve, a heating and cooling device configured to heat and cool the portion of the person, a temperature sensor adapted to be coupled to the person, and a control apparatus coupled to the second end of the tube and having a controller configured to supply a medium through the tube to the sleeve to cause the sleeve to cyclically compress the portion of the person to vasodilate blood vessels in the portion of the person, the controller further being coupled to the heating and cooling device to vary a temperature of the medium in response to a difference in temperature between a preset temperature programmed into the controller and an actual core body temperature of the person as measured by the temperature sensor on the person such that the controller communicates with the heating and cooling device to maintain the core body temperature of the person at substantially the preset temperature.

36. The method claim of claim 1, wherein the step of heating is performed simultaneously with the vasodilating step.

37. The method of claim 1, further comprising the step of providing a heating and cooling device, and the step of one of heating or cooling is performed by using the heating and cooling device.

38. A system for maintaining the core body temperature of a person having a core body, a core body temperature, and blood vessels, the system comprising a pressure applicator configured to apply pressure to a portion of the person to vasodilate blood vessels of the person, a heating device, the heating device being a conductive fabric configured to supply heat to the portion of the person, and a control apparatus coupled to the heating device, the control apparatus having a controller configured to vary the amount of heat supplied by the heating device by regulating the electrical voltage supplied to the conductive fabric in response to a difference in temperature between a preset temperature programmed into the controller and an actual core body temperature of the person received by the controller from the temperature sensor on the person so that the controller maintains the actual core body temperature of the person at substantially the preset temperature.

* * * * *